United States Patent [19]
Fleming et al.

[11] Patent Number: 5,337,611
[45] Date of Patent: Aug. 16, 1994

[54] METHOD OF SIMULATING ULTRASONIC INSPECTION OF FLAWS

[75] Inventors: Marvin F. Fleming, Los Altos; Samuel Hersh, Danville; Soung-Nan Liu, Fremont, all of Calif.

[73] Assignee: Electric Power Research Institute, Palo Alto, Calif.

[21] Appl. No.: 986,153

[22] Filed: Dec. 2, 1992

[51] Int. Cl.⁵ .................................... G01N 29/00
[52] U.S. Cl. ....................................... 73/622; 73/632
[58] Field of Search .................. 376/252, 249; 73/622, 73/632, 530

[56] References Cited

U.S. PATENT DOCUMENTS

| | | | |
|---|---|---|---|
| 3,063,290 | 11/1962 | Kaserman et al. | 376/252 |
| 3,753,852 | 8/1973 | Scott et al. | 376/252 |
| 3,855,847 | 12/1974 | Leschek | 73/71.4 |
| 4,150,577 | 4/1979 | Fetheroff | 73/611 |
| 4,160,386 | 7/1979 | Jackson et al. | 73/625 |
| 4,434,660 | 3/1984 | Michaels et al. | 73/622 |
| 4,470,304 | 9/1984 | Nusbickel, Jr. et al. | 73/611 |
| 4,472,971 | 9/1984 | Marini et al. | 73/587 |
| 4,597,294 | 7/1986 | Brill et al. | 73/623 |
| 4,760,737 | 8/1988 | Kupperman | 73/622 |
| 4,867,168 | 9/1989 | Stoor | 128/653 |
| 5,066,452 | 11/1991 | Hancock et al. | 376/252 |
| 5,115,672 | 5/1992 | McShane et al. | 73/596 |

OTHER PUBLICATIONS

EPRI Technical Brief RPT 301-1: INTRASPECT: An Automated Ultrasonic Imaging System for BWR Piper Inspection; Nov. 1984.

Primary Examiner—Donald P. Walsh
Assistant Examiner—Meena Chelliah
Attorney, Agent, or Firm—Flehr, Hohbach, Test, Albritton & Herbert

[57] ABSTRACT

A method for simulating in real-time the ultrasonic inspection of flaws in power plant components such as piping stores the X, Y and skew data relating to a specific waveform and a specific flaw in a unique format in a multi-disk rotational data storage. The skew angles are respectively stored on one side of a disk with the X-axis data relating to tracks on the disk and the Y-axis data to sectors on the disk. In this manner waveform data of several bytes which represent a defect or flaw can be retrieved and displayed to the user of this simulation system. A RAM is utilized as a cache memory.

7 Claims, 6 Drawing Sheets

FIG.−2

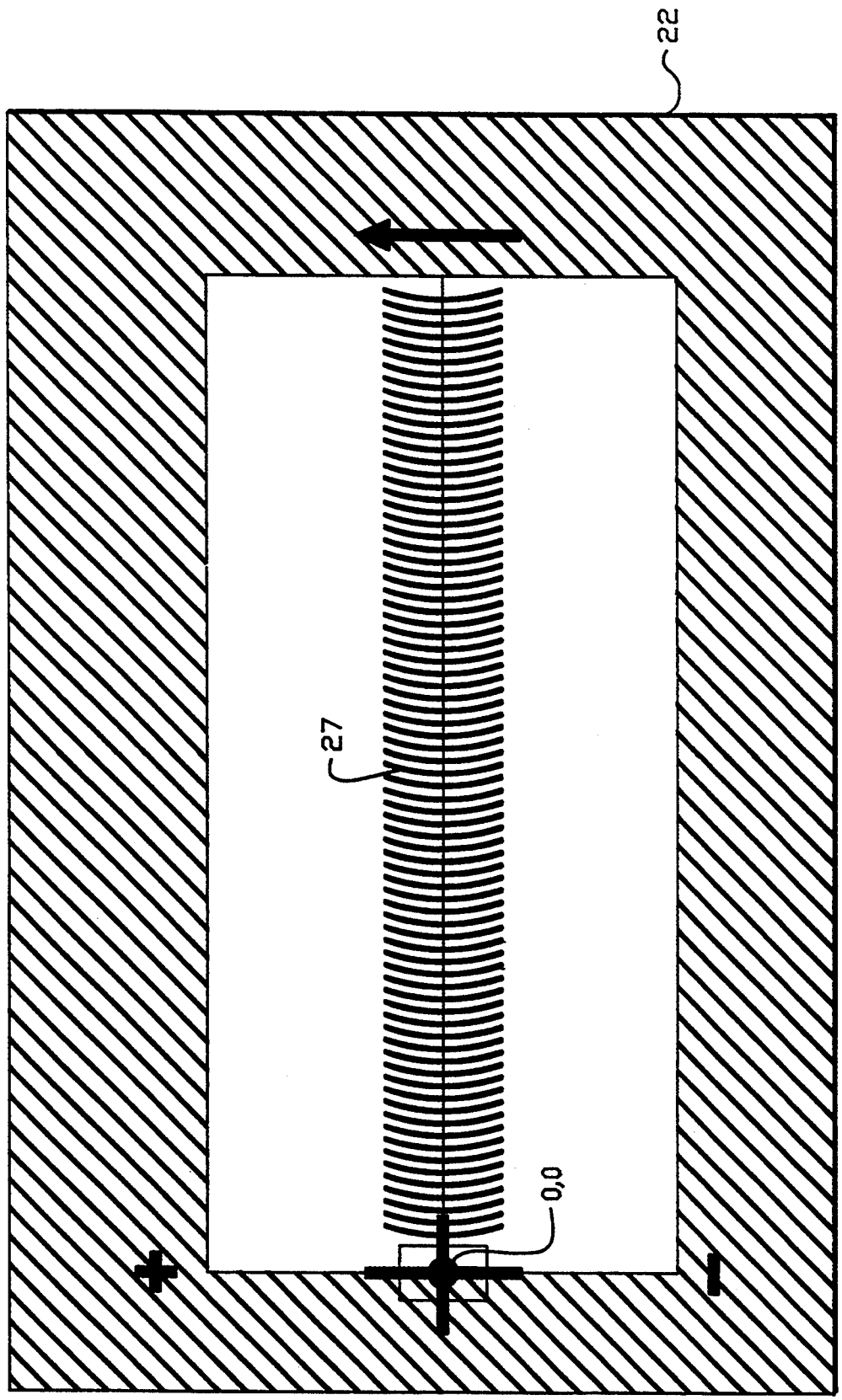
FIG.—4

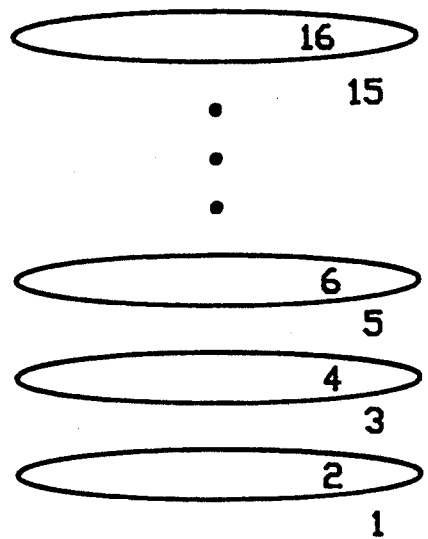
FIG.—5A
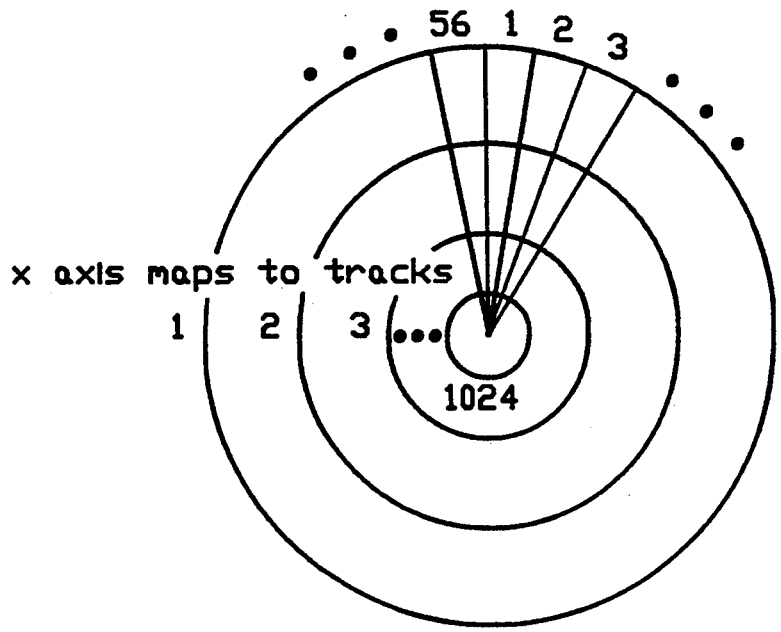
FIG.—5B

METHOD OF SIMULATING ULTRASONIC INSPECTION OF FLAWS

FIELD OF INVENTION

The present invention relates to a method of simulating the ultrasonic inspection of flaws and more particularly of flaws in power plant components such as the piping in a nuclear power plant.

BACKGROUND OF THE INVENTION

As disclosed by the Stoor U.S. Pat. No. 4,867,168, in the past training of personnel for the inspection of flaws has been done with the aid of test blocks having artificially implanted defects where the trainees carry out the scanning of the block with a conventional ultrasonic probe. To remedy the defects of this procedure, the Stoor patent stores in memory actual inspection data gained from scanning a structure containing defects. Such data in the form of ultrasonic waveforms are then retrieved on an X, Y coordinate basis when a simulated transducer or probe is scanned over a test body.

The foregoing technique is a significant improvement over the previous technique of utilizing actual test blocks containing flaws. However, the technique of the Stoor patent does not come close to duplicating an actual ultrasonic inspection. One of the reasons is the time delay in retrieving the data from the memory; in other words, a real time type of display is preferred. Another problem was the lack of a simulation of skew angle (around the Z axis) along with the X and Y position of the ultrasonic transducer.

OBJECT AND SUMMARY OF THE INVENTION

It is therefore an object of the present invention to provide an improved method for simulating the ultrasonic inspection of flaws.

In accordance with the above method there is provided a method of simulating in real-time the ultrasonic inspection of flaws in power plant components such as piping where each flaw is represented by a position sensitive ultrasonic signal waveform having X, Y, and skew angle components relative to an ultrasonic transducer, with skew angle being angular rotation of the transducer about a Z axis orthogonal to the X and Y axes, and where the user moves a position encoder over a simulation test block, the position encoder simulating the movement of an ultrasonic transducer over a real or test piece with flaws, the encoder providing the X, Y and skew components related to a specific waveform. The method comprises storing on a plurality of rotational multi-disk data storage media the X, Y and skew angle data, each skew angle being stored on a respective side of one disk of the multi-disk rotational storage media, with the X axis location relating to the tracks of the disk, and the Y axis relating to the sectors of the disk. The movement of the position encoder is sensed and encoded X, Y, and skew data is read along with waveforms associated with such specific X, Y and skew data from the rotational memory and displayed to the user.

BRIEF DESCRIPTION OF DRAWINGS

FIG. 4 is a top view of a component of the invention shown in FIG. 1.

FIGS. 5A and 5B are respectively side and top diagrammatic views of a disk memory also shown in FIGS. 1 and 2.

Tables 1 and 2 further show the operation of the present invention with regard to generation and storage of a database.

DETAILED DESCRIPTION OF PREFERRED EMBODIMENT

Figure 1:
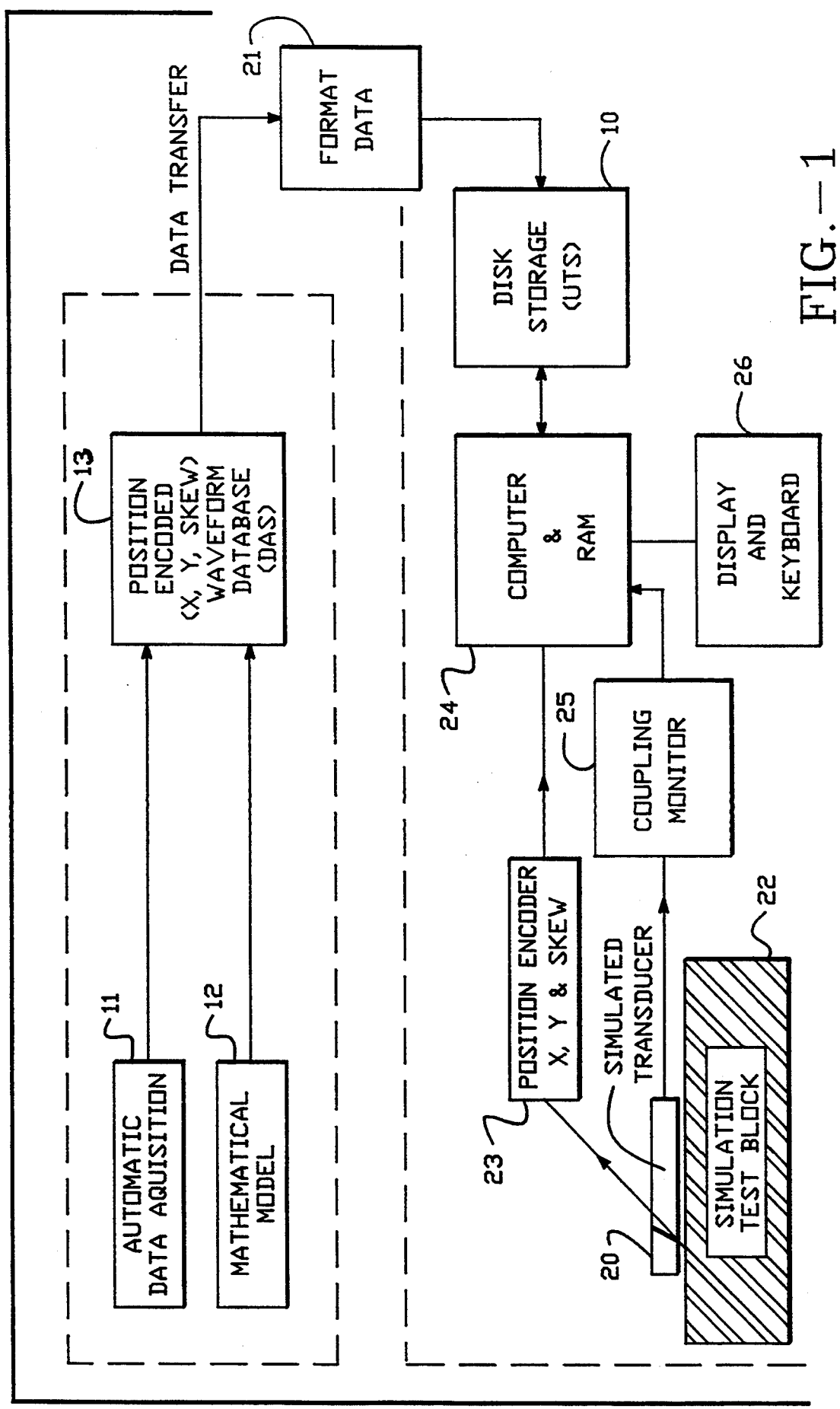
FIG. 1 is a block diagram illustrating the method of the present invention.

FIG. 1 shows the overall block diagram of the present invention where a disk storage unit 10 consisting of, for example, 8 hard memory disks stores ultrasonic signal waveforms which relate to defect data of, for example, piping which was derived from actual specimens known to contain defects. The waveforms are generated either by automatic data acquisition from scanning over a test specimen manufactured with implanted defects or from real life ultrasonic defects which have been recorded. This is indicated at 11. Mathematical models 10 of the ultrasonic signal waveforms may also be provided. These are stored in a data acquisition system (DAS) 13 in the form of a waveform represented by several hundred or thousand bytes of stored data along with X, Y and skew information.

Figure 2:
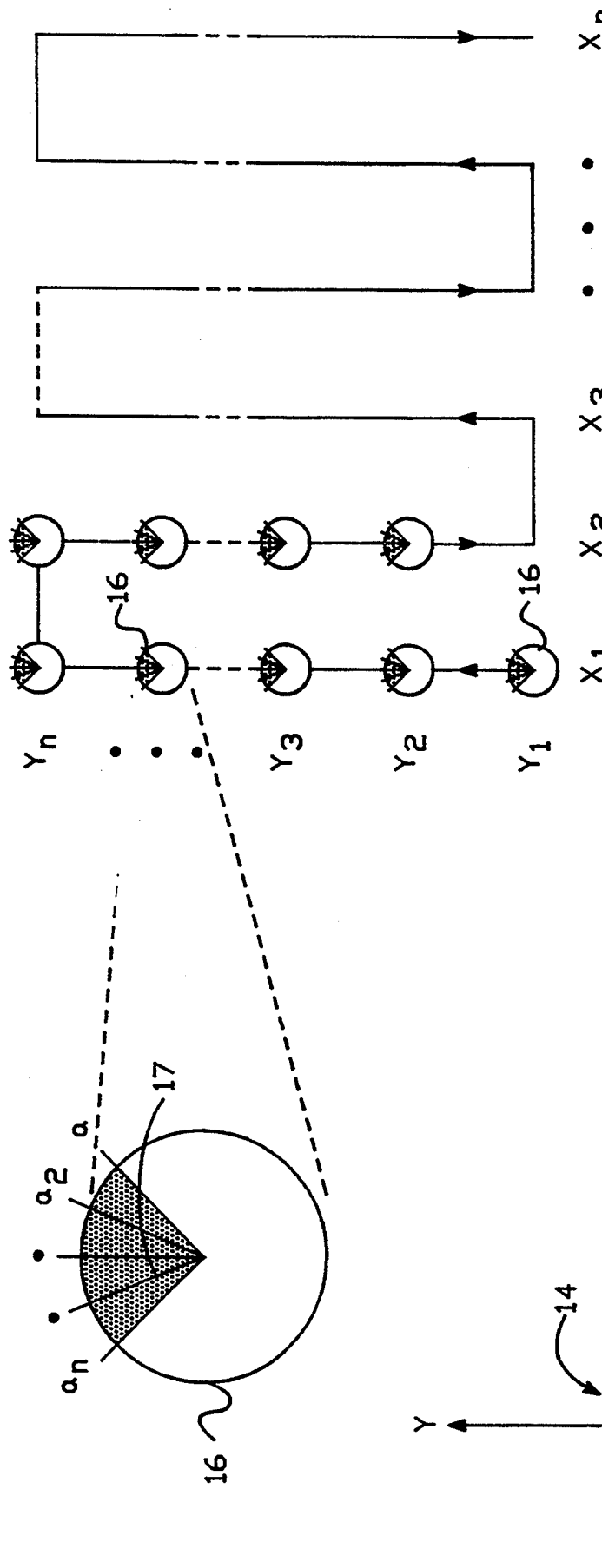
FIG. 2 is a scan pattern diagram illustrating the acquisition of data utilized in FIG. 1.

Referring to FIG. 2 briefly, this illustrates a typical scan pattern for the acquisition of data which may, for example, be accomplished on a specimen containing known defects. The scan starts at the lower lefthand corner of the defect containing specimen at X1, Y1. Such scanning would be done by a typical ultrasonic testing probe (in a manual or automatic data acquisition mode).

In the example illustrated, the scan is bi-directional starting where indicated and proceeds in an up direction indicated by the arrows and then to the X2 position and so on until the end point of the scan is reached. However, data is usually acquired in a unidirectional mode to eliminate the effects of scanner hysteresis back-lash, etc. The relative X, Y axis is shown at 14 along with the Z axis which is where the skew angle is indicated by the angle "a" around the Z axis. The skew is well known in an ultrasonic probe and is in effect the rotation of the probe. Thus referring back to the scan pattern, circle 16 represents a point on the scan pattern in which multiple waveforms are acquired. As shown by the enlarged circle 16', the shaded area 17 represents the range of skew angles from $a_1$ to $a_n$ used to acquire data. From a practical standpoint, such range might start at a positive 10° and go to a negative 10° in two degree steps. And then there is a predetermined interval between the Y positions and the X positions. For example, suitable intervals or increments might be an X increment of 0.250 inches and a Y increment of 0.050 inches. The reason for the smaller Y increment is that generally the Y direction is located on a test specimen to be perpendicular to the defect or the weld. Thus smaller increments are necessary to sufficiently describe such weld or defect. And in accordance with the preferred embodiment of the present invention, it is especially directed to intergranular stress corrosion cracking (IGSCC) in a boiling water reactor (BWR).

Referring back to FIG. 1, after position encoded waveform data is stored in the DAS database 13, it is formatted by the unit 21 and stored in the disk storage unit 10 (to be described in detail below). The inspection training function of the present invention utilizes a simulation test block 22 or actual specimen or mockup over which a position encoder 23 together with a simulation ultrasonic transducer 20 is moved by the operator. The position encoder/transducer is generally in the form of an actual ultrasonic probe to simulate the real experience of inspecting an actual specimen or pipe in the field. Thus the test block may duplicate a pipe shape or an elbow, for example. In addition a coupling monitor 25 may be used to duplicate real conditions where the coupling between specimen and transducer is sensed. When it is moved over the simulation test block 23, the position encoder sends back to the computer and RAM storage device 24, its positional information including X, Y and skew angle data. The computer then accesses disk storage unit 10, and calls up and displays the stored waveforms at that location on display unit 26. Such display unit may be a typical display of a personal computer or the actual field grade ultrasonic testing instrument that an operator or inspector would use or it may do both simultaneously.

The display responds in real-time to the motion of the position encoder or simulated ultrasonic transducer. How this is accomplished is one of the major aspects of the present invention and will be described in detail below.

The present encoder/transducer thus uses a 3-axis scanner rather than a CAD pad to encode transducer position. The benefits are as follows:

1. The same scanner (fitted with motors) may be used for data acquisition and simulation. This permits the user the potential for creating completely new simulations.
2. The scanner may be operated on the actual part, or a facsimile thereof, during simulation.
3. Using the same scanner for both acquisition and simulation eliminates the need to translate transducer position from one coordinate system (acquisition) to another (simulation). This greatly simplifies simulations on parts having a complex surface geometry because the scanner position encoders will output the same values at the same gridpoint during acquisition and simulation regardless of the part geometry.
4. The position encoding resolution of the acquisition data and the simulation data are identical. In general, the optical encoders used in nearly all scanners have significantly greater resolution in the skew axis than, for example, a two-coil CAD pad.
5. It is easier to assure the quality of the simulation because it is possible to directly compare the output of the simulator and the data acquisition system as a function of the scanner for every valid scanner position.

FIG. 4 shows the simulation test block 22 in greater detail. It includes a 0,0 axis point with the Y axis being vertical and the X horizontal. It is generally a stainless steel plate over which the simulated transducer or position encoder is moved. The lining shown at 27 indicates the weld or flaw to be sensed.

As discussed above, it is an important feature of the invention to retrieve and display waveform data on a real-time basis so as to fully simulate an actual inspection. This makes it difficult for the user to tell whether they are using a simulator or are connected to a real transducer reading out actual defects from a test specimen having flaws. The definitions of "real-time" data display rates for a CRT display and a UT (ultrasonic transducer) instrument display are different. Real-time for a CRT display is defined as the normal CRT frame refresh rate which is fixed at about 30 frames, or waveforms, per second. Most UT instruments are analog systems using X-Y vector graphics displays similar to a standard oscilloscope, rather than raster displays. UT instruments have the property that the waveform repetition rate, which is user selectable, is used to control the displayed waveform brightness. Therefore, real-time is defined as the refresh rate controlled by the UT instrument and is typically variable from 100 to at least 1000 waveforms per second.

To achieve the real-time readout of data especially with the incorporation of the skew angle parameter, large amounts of data, for example, 600 megabytes are required for full simulations. Thus there is a problem resolving the large non-random access storage capacity with speed requirements. This is especially true since data are stored serially in mass storage devices. High speed random action storage devices such as solid state memory (RAM) can easily simulate small amounts of ultrasonic data but such small amounts are not useful for the present application. Thus the present invention utilizes a Winchester disk storage unit which has the position encoded data stored in a unique manner to provide for rapid access.

Skew manipulation is often used by UT inspectors employing manual ultrasonic inspection techniques. The effectiveness of skew as a variable is due to the fact that different classes of ultrasonic reflectors respond differently to variations of transducer skew angle. In general, predictions of the response of ultrasonic targets to skew motion have not been useful for training and simulation in typical inspection applications. Therefore, skew may be required to discriminate different classes of flaws from one another and from non-flaws. For example, intergranular stress corrosion cracking (IGSCC) tends to produce a signal response over a larger range of skew angles than does weld counterbore or weld root. Furthermore, the IGSCC tends to produce a signal amplitude may increase as the signal is oscillated into the various facets of the crack whereas the weld root signal tends to decrease as the transducer is skewed from the position that produces the maximum signal response (Source: EPRI NDE Center, Training Module for UT Operator Training for Intergranular Stress Corrosion Cracking, 4/89). Until the interaction of flaw geometry and skew on ultrasonic signals are predictable, it is necessary to record all pertinent skew angles so that this diagnostic information is present in the resulting simulation.

FIGS. 5A and 5B illustrate a disk storage unit 10 and as illustrated in FIG. 5A there are eight disks having 16 surfaces which are designated 1 through 16. FIG. 5B illustrates a single disk surface having 1024 tracks and 56 sectors. Data from the database 13 is reformatted and stored on the disks. The X location relates or maps to the tracks of the disk. Y location data relates or maps to the sectors, and each disk surface represents a single skew angle location. Thus as illustrated in 5A, 16 different skew angles may be represented.

Now referring to Table I (shown below), this shows the storage of 6160 waveforms in the disk storage unit. Each waveform has associated X, Y and skew data location. The table illustrates on what track, what sector, and what surface or "head" the specific multi-byte data of that waveform is stored. Thus the X position 1 relates to track 1 and so on. The Y position is related to sector and the angle to the head or disk surface.

Table II (below) shows how the data from the DAS database unit 13 in FIG. 1 is formatted for proper storage on the Winchester disk unit 10 (the ultrasonic simulator, UTS, database). Initially as shown in step 1, initial head, track and sector numbers are set. Then in step 2, data is read from data acquisition unit system (DAS) database 13 along with the file header in step 3, and the files are sorted by skew angle in ascending order as shown in step 4. Then in step 5 for each skew angle along with the file header the start positions and end positions are read along with the intervals outlined with regard to FIG. 2 along with other parameter data.

Then in step 6 for each waveform, waveform data is read from the database, the X, Y and skew positions determined of a waveform, and the disk head (or surface) and the tracks are determined, by skew and Y data. Then in step 7 the sector is determined for the X-axis and the waveforms are finally written in the location as shown in Table 1, and the file pointer incremented.

Thus since each value of skew data is stored on a separate disk surface and refreshed from its respective surface on the disk, fast access is guaranteed since at least for skew angle, in effect the disk storage is a random access memory. The Y axis is chosen for the sector storage since the fast rotation of the disk provides for rapid retrieval. And this is especially true as discussed above since the Y axis corresponds to ultrasonic data taken when the probe is moved transverse to a flaw. And finally the X axis is least important to retrieve rapidly.

Since the sequential organization of the X storage location along, for example, the 1024 tracks of a disk is important, a Winchester disk type operating system must be chosen where a defective sector does not result in a track which is in a sequentially different position. In other words, the location must not switch to a non-sequential track in the event of a defective track. One such system is sold by Hewlett Packard under the model name ESD I.

In addition, it is quite apparent that the skew angle data may be selected in degree increments to correspond to the type of flaw where the degree increments are fewer over a limited degree range if the flaw is abrupt and vice versa. In some cases the number of disks might have to be increased. Finally to provide for further speed in the operation of the system to give a better, smoother or higher spatial resolution, the computer of the present invention has the capability of extrapolating, for example, between larger values of delta Ys using a weighted average between two adjacent points.

Figure 3:
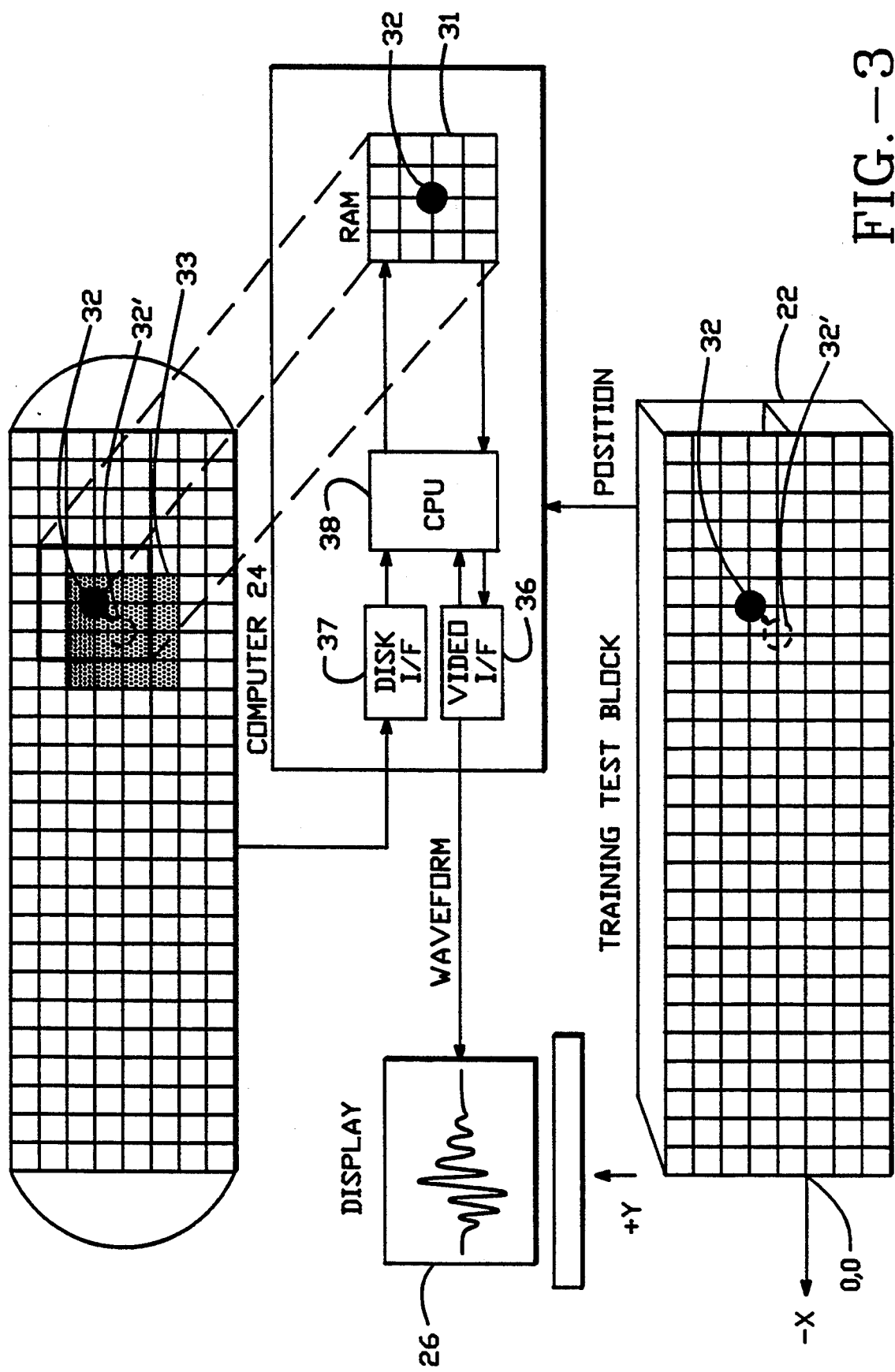
FIG. 3 is a block diagram illustrating a more detailed operation of FIG. 1.

FIG. 3 illustrates another important aspect of the invention where a virtual cache memory is provided by the RAM unit 31 which is part of computer 24. An amount of data is stored in the RAM 31 to allow the simulator to respond to small movements of the probe. As shown, assuming the probe is at a data point 32, the organizational algorithm used for storage of this data in the RAM is best understood as being stored on a cylinder so that positive or negative movements are managed. In other words, as illustrated in FIG. 3, all of the data surrounding data point 32 are also supplied to the RAM so that if the probe moves to the position shown at 32'for example, then the surrounding information in the disk memory shown by the shaded square area 33, will be moved to the RAM. The square area 33 can be thought of as a page. Referring to the other aspects of FIG. 3, display 26 illustrates a typical waveform from the video interface unit 36. Interface with the disk 10 is provided by unit 37 and the computer 24 of course includes a CPU 38.

Although a "page" type virtual cache algorithm is illustrated, from a practical standpoint, the caching system may be accomplished using a commercial third party program called SMARTDRV SYS supplied with microsoft MS-DOS 5.00. Because data are organized on the magnetic hard disk so that each track contains all of the waveforms for a single scan line for Y (at a given skew) and because the disk has its own internal track cache which causes any request to read an entire track into the disk track cache if it is not already there, there is effectively obtained the result similar to that shown in FIG. 3. Thus a page can be redefined as including all of the data on a particular Y scan line on the track of a disk.

Figure 6:
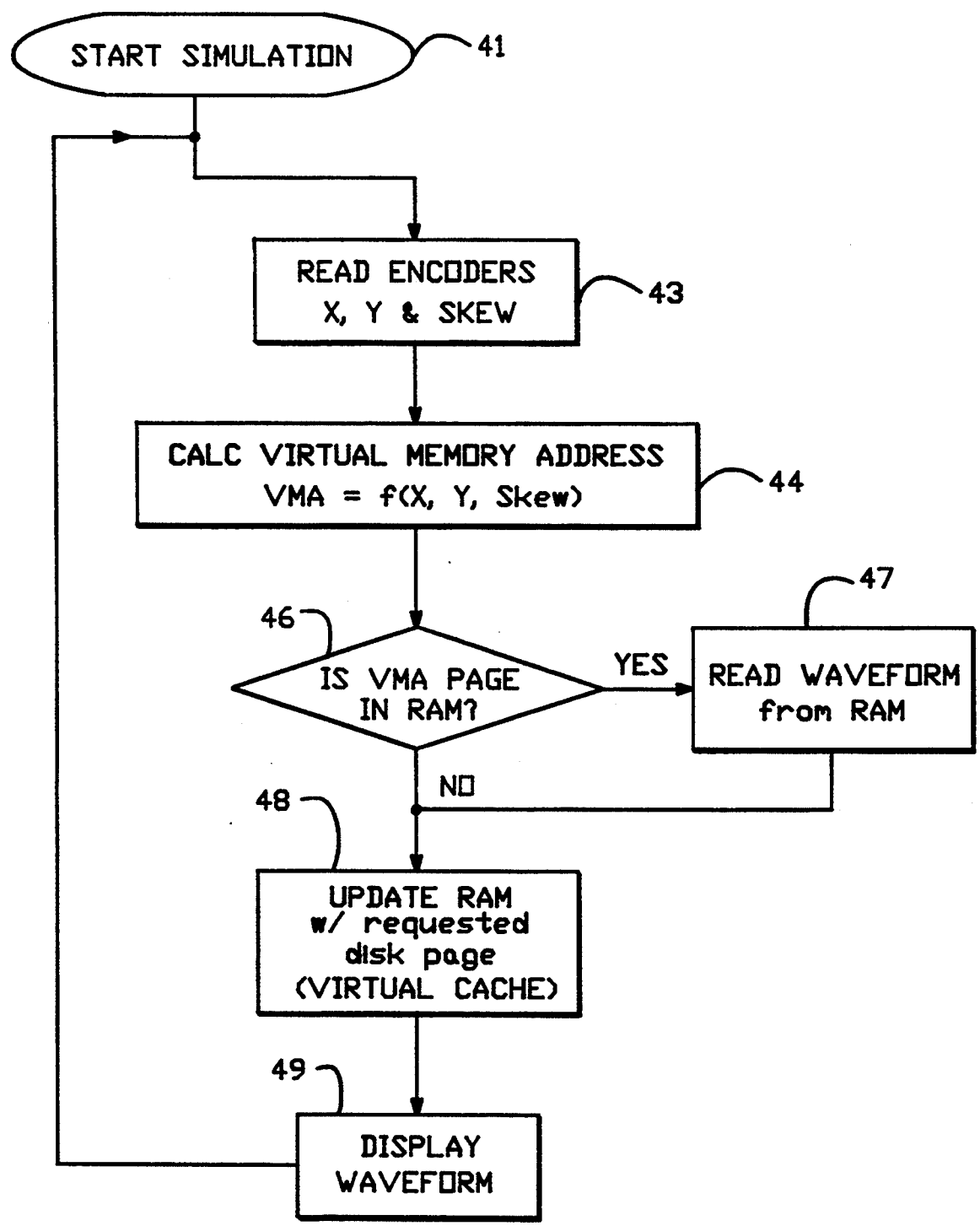
FIG. 6 is a flow chart showing the operation of the present invention.

The overall simulation method of the present invention is outlined in broad detail in the flow chart of FIG. 6. And also referring to FIG. 3 a simulation is started in step 41 by the computer. Then the position encoder's X, Y and skew angle are read in step 43 and the virtual memory address in the RAM memory calculated. Referring to Table I, this would be the track, sector, and head location. After step 44, the question is asked in step 46 is this virtual memory address a page in the RAM 31. If so, in step 47, the waveform is read. If not, the RAM in step 48 is updated and then in step 49 the waveform is displayed, and the process is started again in readiness for the next movement of the simulator head or position encoder.

With the above technique for managing the waveform data, a steady data rate is accomplished so that waveforms are displayed at speeds faster than the human perception can distinguish variations. The Winchester type disk and the formatting of stored data so that each disk surface represents skew values and with the X and Y positions being the track and sectors respectively of a particular disk surface, this allows values including skew to be recalled at high speeds. In fact, only nanoseconds which is the time required to switch to a different head or a different surface. The cache RAM memory allows the simulator to rapidly respond to any movements of the transducer probe. The size of the RAM is adjusted to provide sufficient memory for the highest movement speeds at which an operator could absorb the data.

In addition or alternatively the inherent track cache memory of the Winchester disk can also be utilized. In any case the above algorithm provides a smooth refreshing of the ultrasonic waveforms. Thus an improved method of simulating the ultrasonic inspection of flaws in power plant components has been provided.

What is claimed is:

1. A method of simulating in real-time the ultrasonic inspection of flaws in electric utility generating station components such as piping where each flaw is represented by a position sensitive ultrasonic signal waveform having X, Y and skew angle components relative to an ultrasonic transducer, with skew angle being angular rotation of the transducer about a Z axis orthogonal to the X and Y axes, and where the user moves a position encoder over a simulation test block, the position encoder simulating the movement of an ultrasonic transducer over a real or test piece with flaws, the encoder providing the X, Y and skew position components related to a specific waveform, said method comprising the following steps:

storing on a plurality of rotational multi-disk data storage media said X Y and skew angle related waveform data, each skew angle being located on a respective side of one disk of said rotational storage media, with the X axis location relating to the tracks of the disk and the Y axis location relating to the sectors of the disk;

sensing the movement of said position encoder head and reading encoded X, Y, and skew data and reading waveforms associated with such specific X, Y and skew data from said rotational memory and displaying to said user.

2. A method as in claim 1 where in said reading step a virtual memory is created for X, Y, and skew waveform data by downloading data from said rotational disk storage to a random access memory (RAM) as a page where a page comprises X, Y, and skew data of a specific location and surrounding data, and in response to movement of said position encoder downloading a new page to said RAM;

and at substantially the same time reading and displaying waveforms from said RAM for said specified X, Y, and skew data.

3. A method as in claim 1 including the step of extrapolating delta Ys by using a weighted average between two adjacent points of Y data.

4. A method as in claim 1 where the location of stored data on a said rotational disk is controlled so as not to switch to a nonsequential track in the event of a defective track.

5. A method as in claim 1 where said position encoder includes a simulated ultrasonic transducer which is capable of acquiring real ultrasonic data.

6. A method as in claim 5 including the step of monitoring the coupling of said transducer to said test piece.

7. A method as in claim 1 where said Y axis data corresponds to ultrasonic data taken while moving transverse to a flaw.

* * * * *